(12) United States Patent
Chainer et al.

(10) Patent No.: US 6,249,399 B1
(45) Date of Patent: Jun. 19, 2001

(54) METHODS AND SYSTEMS FOR SELF-SERVOWRITING INCLUDING MAINTAINING A REFERENCE LEVEL WITHIN A USEABLE DYNAMIC RANGE

(75) Inventors: Timothy Joseph Chainer, Mahopac; Mark Delorman Schultz, Elmsford; Bucknell Chapman Webb, Ossining; Edward John Yarmchuk, Somers, all of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/416,289

(22) Filed: Oct. 14, 1999

Related U.S. Application Data

(62) Division of application No. 09/045,429, filed on Mar. 20, 1998, now Pat. No. 6,031,680, which is a division of application No. 08/654,950, filed on May 29, 1996, now Pat. No. 5,757,574.

(51) Int. Cl.[7] .................................. G11B 21/02

(52) U.S. Cl. ............................................. 360/75

(58) Field of Search ........................ 360/75, 77.04, 360/113, 77.02, 77.05, 77.07, 77.08

(56) References Cited

U.S. PATENT DOCUMENTS

| 4,414,589 | 11/1983 | Oliver et al. ............ 360/77.08 X |
|---|---|---|
| 4,912,576 | 3/1990 | Janz ........................... 360/75 X |
| 5,193,034 | 3/1993 | Tsuyoshi et al. ......... 360/77.08 X |
| 5,270,886 | * 12/1993 | Nigam ........................ 360/78.05 |
| 5,375,020 | 12/1994 | Aggarwal et al. ............... 360/75 |
| 5,416,652 | 5/1995 | Lewis ..................... 360/77.02 X |
| 5,541,784 | 7/1996 | Cribbs et al. .................... 360/75 |
| 5,570,247 | 10/1996 | Brown et al. ................... 360/75 |
| 5,612,833 | 3/1997 | Yarmchuk et al. .............. 360/75 |
| 5,615,058 | 3/1997 | Chainer et al. ................. 360/51 |
| 5,757,574 | 5/1998 | Chainer ......................... 360/75 |

FOREIGN PATENT DOCUMENTS

WO 94/11864  5/1994  (WO) .

* cited by examiner

*Primary Examiner*—David Hudspeth
*Assistant Examiner*—James L Habermehl
(74) *Attorney, Agent, or Firm*—Heslin & Rothenberg, P.C.

(57) ABSTRACT

Methods and systems for self-servowriting a data storage medium are disclosed, including servoing to propagation bursts of a propagation pattern located in tracks other than an immediately preceding track. Reference levels used to position a recording head are accordingly kept in a usable dynamic range necessary to keep servo track spacing constant across the medium. The methods and systems are disclosed in connection with a rotary actuator having spaced read and write heads. Similar methods are disclosed for writing trigger or timing bursts of the propagation pattern.

6 Claims, 9 Drawing Sheets fig. 1a fig. 1b fig. 2a fig. 2b fig. 2c fig. 3a fig. 3b fig. 3c fig. 3d fig. 3e fig. 4 fig. 5 fig. 6 fig. 7 fig. 8a fig. 8b

METHODS AND SYSTEMS FOR SELF-SERVOWRITING INCLUDING MAINTAINING A REFERENCE LEVEL WITHIN A USEABLE DYNAMIC RANGE

CROSS-REFERENCE TO RELATED APPLICATIONS

This application is a division of U.S. patent application Ser. No. 09/045,479, filed Mar. 20, 1998 now U.S. Pat. No. 6,031,680, which itself is a division of U.S. patent application Ser. No. 08/654,950, filed May 29, 1996, now U.S. Pat. No. 5,757,574.

This application is related to the following commonly owned United States Patent Applications:

U.S. Ser. No. 08/028,044 of T. Chainer et al. filed on Mar. 8, 1993 entitled "A Method and System for Writing a Servo-Pattern on a Storage Medium;"

U.S. Ser. No. 08/348,773 of T. Chainer et al., filed on Dec. 1, 1994 entitled "Improvements in Self-Servowriting Timing Pattern Generation;" and U.S. Ser. No. 08/349,028 of E. Yarmchuk et al., filed on Dec. 2, 1994 entitled "Radial Self-Propagation Pattern Generation for Disk File Servowriting."

Each of these applications is hereby incorporated by reference herein in its entirety.

FIELD OF THE INVENTION

This invention relates generally to storage devices for computers. More particularly, it relates to a disk drive apparatus, and to a method for writing servo information therein.

BACKGROUND OF THE INVENTION

Increased levels of storage capacity in floppy and hard disk drives are a direct result of the higher track densities possible with voice-coil and other types of servo positioners. Previously, low track density disk drives were able to achieve satisfactory head positioning with leadscrew and stepper motor mechanisms. However, when track densities are so great that the mechanical error of a leadscrew-stepper motor combination is significant compared to track-to-track spacing, an embedded servo-pattern is needed so that the position of the head can be determined from the signals it reads.

Conventional hard disk manufacturing techniques often include writing servo-patterns on the media of a head disk assembly (HDA) with a specialized servowriter instrument. Laser positioning feedback is used in such instruments to read the actual physical position of a recording head used to write the servo-patterns. Unfortunately, it is becoming more and more difficult for such servowriters to invade the internal environment of an HDA for servowriting because the HDAs themselves are exceedingly small and depend on their in-place covers and castings for proper operation. Some HDAs are the size and thickness of a plastic credit card. At such levels of microminiaturization, traditional servowriting methods are inadequate.

Conventional signals of servo-patterns typically comprise short bursts of a constant frequency signal, very precisely located offset from a data track's center line, on either side. The bursts are generally, but not required to be, located in a trajectory within a track. The bursts are written in a sector header area, and can be used to find the center line of a track. Staying on center is required during both reading and writing. Since there can be sixty, or even more, sectors per track, that same number of servo-pattern areas must be dispersed around a data track. These servo-pattern areas allow a head to follow a track center line around a disk, even when the track is out of round, as can occur with spindle wobble, disk slip and/or thermal expansion. As technology advances provide smaller disk drives, and increased track densities, the placement of servo-patterns must also be proportionately more accurate.

Servo-patterns are conventionally written by dedicated, external servowriting equipment, and typically involve the use of large granite blocks to support the disk drive and quiet outside vibration effects. An auxiliary clock head is inserted onto the surface of the recording disk and is used to write a reference timing pattern. An external head/arm positioner with a very accurate lead screw and a laser displacement measurement device for positional feedback is used to precisely determine transducer location and is the basis for burst placement and spacing of bursts in successive tracks. The servowriter requires a clean room environment, as the disk and heads will be exposed to the environment to allow the access of the external head and actuator.

U.S. Pat. No. 4,414,589 to Oliver et al. describes servowriting wherein optimum track spacing is determined by positioning one of the moving read/write heads at a first limit stop in the range of travel of the positioning means. A first reference burst is then written with the moving head. A predetermined reduction number or percentage of amplitude reduction X %, is then chosen that is empirically related to the desired average track density. The first reference burst is then read with the moving head. The moving head is then displaced away from the first limit stop until the amplitude of the first reference burst is reduced to X % of its original amplitude. A second reference burst is then written with the moving head and the moving head is then displaced again in the same direction until the amplitude of the second reference burst is reduced to X % of its original value. The process is continued, writing successive reference bursts located in successive tracks and displacing the moving head by an amount sufficient to reduce the amplitude to X % of its original value, until the disk is filled with reference bursts in tracks (i.e., a propagation pattern). The number of reference bursts so written is counted and the process is stopped when a second limit stop in the range of travel of the positioning means is encountered. Knowing the number of tracks written and the length of travel of the moving head, the average track density is checked to insure that it is within a predetermined range of the desired average track density. If the average track density is high, the disk is erased, the X % value is lowered and the process is repeated. If the average track density is low, the disk is erased, the X % value is increased and the process is repeated. If the average track density is within the predetermined range of the desired average track density, the desired reduction rate X %, for a given average track density, has been determined and the servowriter may then proceed to the servowriting steps, using the collection of reference bursts written as a propagation pattern. This technique cannot accommodate changes in reference levels which may be required across the disk surface.

The process of servowriting using only the internal recording transducer and product actuator, (one form of self-servowriting) is thus generally known to involve a somewhat rigid application of three largely distinct subprocesses: writing and reading magnetic bursts to provide precise timing; positioning the recording transducer at a sequence of radial locations using the variation in readback signal amplitude from propagation bursts as a sensitive position transducer; and writing the actual product servo-pattern at the times and radial locations defined by the first two subprocesses. Again, such techniques currently suffer from exposure to changing conditions across the disk surface, and, in addition, to manufacturing tolerances in the HDAs themselves.

What is required are systems and methods for self-servowriting which are more flexible and which overcome the deficiencies of the presently known self-servowriting techniques.

SUMMARY OF THE INVENTION

Briefly summarized, the present invention, in one aspect, is a method and system for writing propagation bursts in a self-servowriting system. The system has a storage medium with a plurality of tracks for holding bursts therein. The method and system include servoing to a first propagation burst located in a first track in the plurality of tracks, and writing a second propagation burst in a second track of the plurality of tracks while servoing to the first propagation burst. The first track does not immediately precede the second track.

The first track may succeed the second track, in which case the method and system may further include servoing to a third propagation burst located in a third track of the plurality of tracks, and writing the first propagation burst in the first track while servoing to the third propagation burst, wherein the third track precedes the second track.

The first track may precede the second track (i.e., there is at least one track between the first track and the second track) in which case the first track may be the penultimate preceding track relative to the second track.

The method and system may also include servoing to a plurality of propagation bursts, including the first propagation burst, located in respective tracks of the plurality of tracks. In this case, the writing may include writing the second propagation burst while servoing to the plurality of propagation bursts. Further, the servoing may include deriving a function from signals received from the plurality of propagation bursts, and the function may be a weighted average calculated from the signals.

In another aspect, the present invention is a method and system for writing product servo-pattern bursts in a self-servowriting system having a storage medium with a plurality of tracks for holding bursts therein. The method and system include writing a first product servo-pattern burst in a first track of the plurality of tracks. The method and system further include writing a second sequential product servo-pattern burst in a second track of the plurality of tracks while servoing to a third propagation burst located in a third track. The third track is located intermediate the first track and the second track. There may be a plurality of propagation bursts located in respective tracks of multiple tracks of the plurality of tracks. In this case, the multiple tracks include the third track and are located intermediate the first track and the second track in which the sequential product servo-pattern bursts are written.

In yet another aspect, the above-described positioning sequences may be combined in a method and system for keeping a reference signal level in a usable dynamic range. The reference signal level is used to position a write head while writing a propagation pattern on a surface of a storage medium of a self-servowriting system. The method and system include using a first positioning sequence for reading and writing a first portion of propagation bursts of the propagation pattern over a first region of the surface. The method and system further include using a second, different positioning sequence for reading and writing a second portion of propagation bursts of the propagation pattern over a second region of the surface. The reference signal level is thereby kept in the usable dynamic range for positioning said write head while writing the first and second portions of the propagation pattern.

In still another aspect, the present invention includes a method for writing timing and positioning bursts of a propagation pattern in a self-servowriting system. The system may have a storage medium with a plurality of tracks for holding bursts therein. The method and system include writing a plurality of successive propagation bursts comprising a portion of the propagation pattern in first respective tracks separated by a first track pitch. Further, a plurality of successive timing bursts are written comprising said portion of the propagation pattern in second respective tracks of the plurality of tracks. The second respective tracks are separated by a track pitch different than the first track pitch. At least one of the first respective tracks may comprise at least one of the second respective tracks.

The above-described methods and systems are especially useful in a self-servowriting storage system having a circular medium with a plurality of radial tracks therein, and wherein a rotary actuator is used to self-servowrite the medium.

By employing the methods and systems of the present invention, changes in reference levels can be accommodated across the medium surface, thereby. compensating for changing self-servowriting conditions across the disk surface, including compensating for manufacturing tolerances in spaced read and write heads and the skew angle of a rotary actuator.

DESCRIPTION OF THE DRAWINGS

The subject matter regarded as the present invention is particularly pointed out and distinctly claimed in the concluding portion of the specification. The invention, however, both as to organization and method of practice, together with further objects and advantages thereof, may best be understood by reference to the following detailed description of the invention and the accompanying drawings in which:

FIG. 3b depicts the resulting offset between the read and write elements for the rotary actuator of FIG. 3a;

DETAILED DESCRIPTION OF THE INVENTION

The inventors of the present invention have discovered that the shortcomings of the previously described techniques are especially problematic if considered in connection with the use of modern magneto-resistive heads which use separate magneto-resistive read and inductive write heads. For recording heads in which the read and write elements are physically separate, the dynamic range of radial displacement is a function of the read and write widths and the relative offset of the read to write element. Further, when used in combination with rotary actuators, the offset also becomes a function of the angular position of the actuator. Unfortunately, for certain combinations of the above parameters, the radial displacement required may not be achievable within the usable dynamic range of a reference level used to position the actuator. The prior techniques do not address separate read and write elements, on rotary actuators, and the resulting dynamic range limit. This invention overcomes these limitations by proposing alternative propagation positioning techniques.

Self-servowriting, when used herein, connotes generally using the medium itself, and propagation patterns thereon, to position the head during writing of the product servo-pattern. Although in preferred embodiments the same head system is used to write the propagation patterns, product servo-patterns, and read and write data on the medium; other self-servowriting systems may include separate head systems for writing the propagation patterns, product servo-patterns, and reading and writing data on the medium.

Figure 1A:
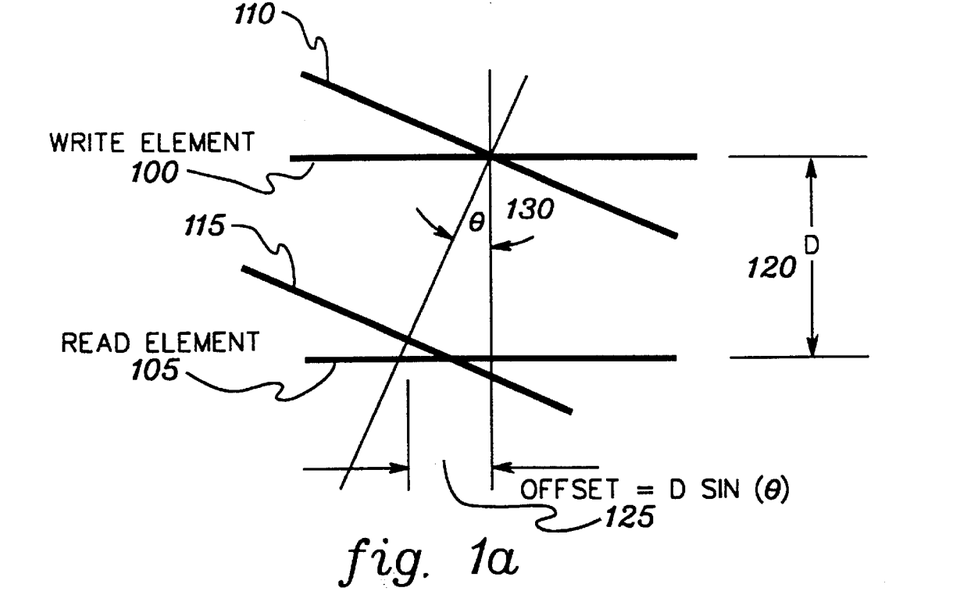
FIG. 1a depicts two positions of a magneto-resistive read and write element pair possible in a rotary actuator system.

Magneto-resistive recording heads used in current disk drive designs may have separate read and write elements or heads as shown in FIG. 1a. The read 105 and write 100 elements typically have different widths and are physically separated by a distance D 120. When these heads are used in combination with modern rotary actuators in exemplary positions 115 and 110 respectively, the read and write offset 125 changes due to the skew angle 130 of the head to track resulting from the angular rotation of the actuator and the physical distance D 120 between the elements. The offset is given by:

$$\text{Offset} = D \sin(\Theta)$$

Figure 1B:
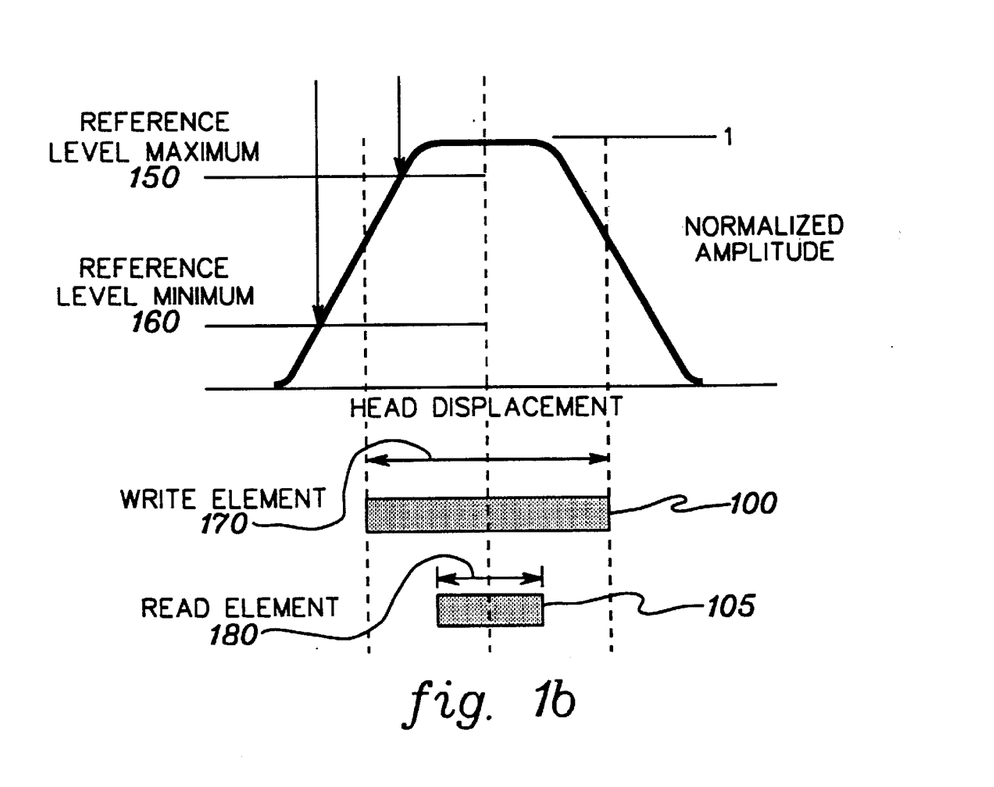
FIG. 1b depicts read element amplitude changes from an on-track to off-track position.

In the propagation of bursts, the read element is servoed to the edge of an amplitude burst. A position signal is obtained by measuring the normalized read head amplitude. The head is servoed to a predetermined percentage (i.e., "reference level") of the on-track amplitude which displaces the head radially with respect to the propagation burst centers. As shown in FIG. 1b the normalized read element amplitude changes approximately linearly from 1 when on-track to 0 when the read element is completely off-track. In practice there are limits on the minimum and maximum reference levels required to provide a position signal for the servo system which we will refer to as Reference Level Maximum 150 and Reference Level Minimum 160. The radial displacement (in this embodiment measured along the trajectory of the actuator) corresponding to a change in amplitude is a function of the difference in the write element width 170 and the read element width 180 and also the offset 125 between the centers of the read and write elements as shown in FIG. 1a. In addition, there may also be an offset between the write and read elements built into the head design at the time of manufacture, and/or other manufacturing tolerances which aggravate the self-servowrite problems discussed above.

In the above-identified U.S. Patent Application entitled "RADIAL SELF-PROPAGATION PATTERN GENERATION FOR DISK FILE SERVOWRITING," a technique is disclosed to adjust the reference level across the disk surface to maintain proper track spacing. However, that application does not address any techniques to overcome the absolute maximum and minimum levels discussed herein.

There are two ranges of motion which can be calculated from the dynamic range of the on-track amplitude referred to respectively as the MinimumMove and the MaximumMove.

Figure 2A:
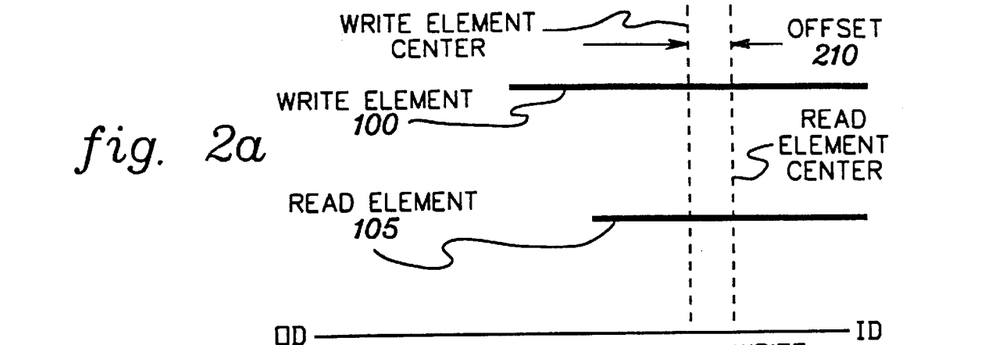
FIG. 2a depicts a manufactured offset possible between the centers of read and write elements.
Figure 2B:
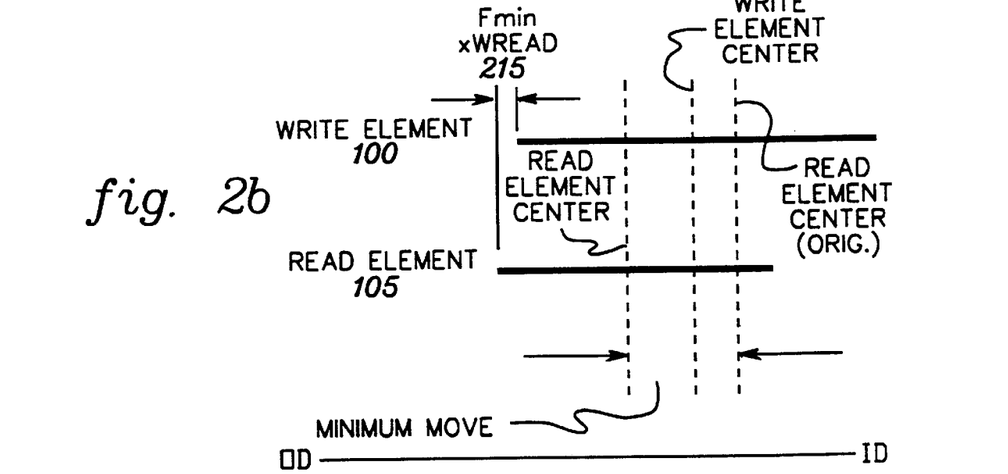
FIG. 2b depicts displacing a read element just enough to reduce the read back amplitude to a reference level maximum.

The case of propagation of the pattern from inside diameter ("ID") to outside diameter ("OD") is described, but similar equations can be written from the OD to ID. In either case, the tracks in which the propagation patterns and servo-patterns are written can be considered to be arranged successively relative to this general direction of propagation across the disk surface. The offset is defined as positive if the read element center is displaced towards the OD relative to the center of the write element. The MinimumMove corresponds to the minimum displacement the read head will undergo corresponding to the minimum change in read signal amplitude from the on-track value. As shown in FIG. 2a, a dual element head may have a manufactured offset 210. The MinimumMove distance shown in FIG. 2b corresponds to displacing the read element 105 just enough to reduce the readback amplitude to the Reference Level Maximum to allow servoing of the head to the edge of the propagation burst track. As shown in FIG. 2b the MinimumMove distance is given by $$MinimumMove = \frac{(W_{write} - W_{read})}{2} - \text{Offset} + (F_{min})W_{read}$$

where $W_{write}$ is the write width, $W_{read}$ is the read width, and $(F_{min}) W_{read}$ (215) is the fraction of the read element width which is displaced beyond the edge of the written amplitude burst.

Figure 2C:
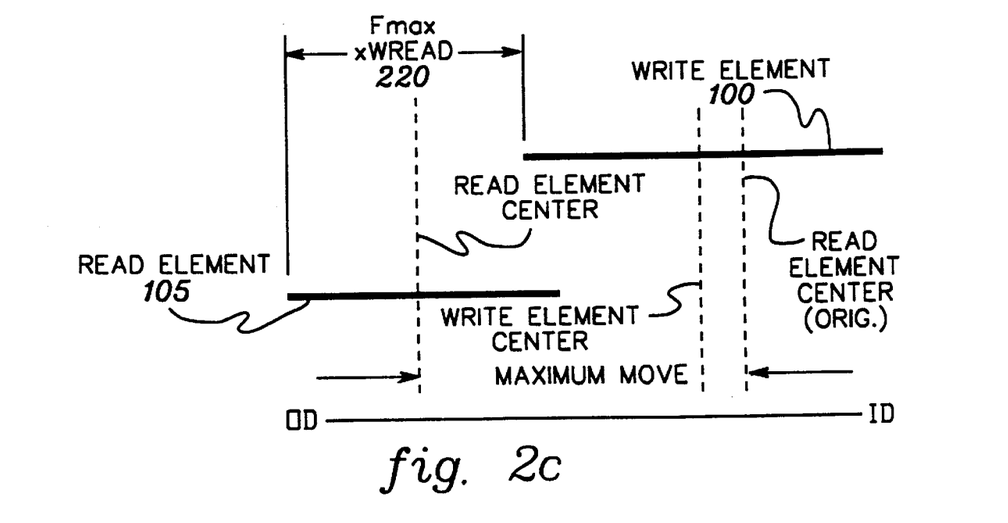
FIG. 2c depicts displacing the read element just enough to reduce the read back amplitude to a reference level minimum.

The MaximumMove as shown in FIG. 2c corresponds to the maximum displacement the head will undergo corresponding to reducing the head readback amplitude to the Reference Level Minimum. This can similarly be shown to be given by:

$$MaximumMove = \frac{(W_{write} - W_{read})}{2} - \text{Offset} + (F_{max})W_{read}$$

where $(F_{max}) W_{read}$ (220) is the fraction of the read element width which is displaced.

Figure 3A:
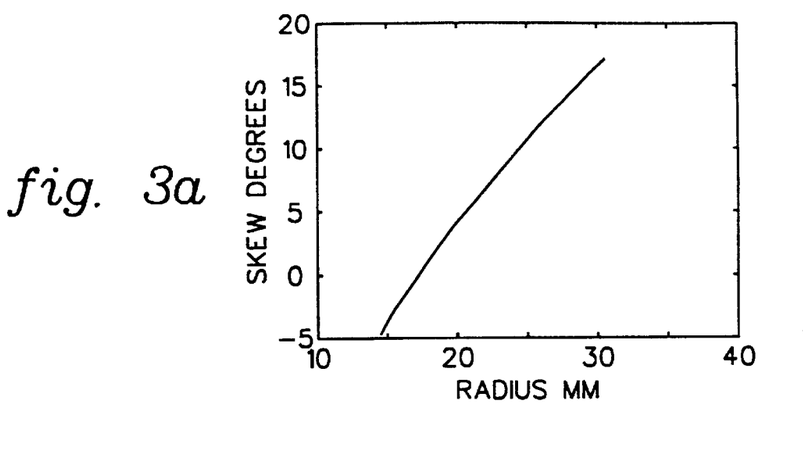
FIG. 3a depicts a typical skew angle for a typical rotary actuator across a disk surface.
Figure 3B:
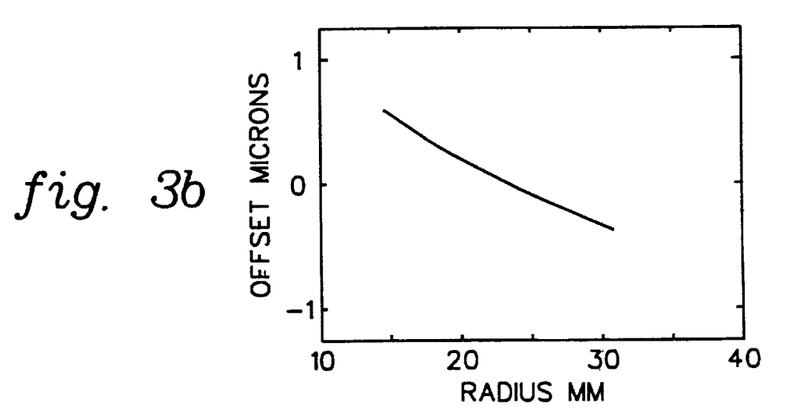

For linear actuators the offset is a constant and therefore the MinimumMove and MaximumMove distances are fixed for the entire data band. However, in the case of rotary actuators, the offset is a function of radial position, therefore the Minimum and MaximumMove distance will depend on the radial location of the head. The skew angle for a typical rotatory actuator shown in FIG. 3a has a change of skew angle of −5 to 17 degrees when the rotary actuator moves from the ID to the OD data track over the surface. (Assuming a write width of 3.1 μm and a read width of 2.3 μm and a write-to-read element distance of 3.6 μm.) This results in an offset of the read and write elements which is plotted in FIG. 3b and shows a shift in the read/write offset of approximately 1.3 microns from the ID to OD.

Figure 3C:
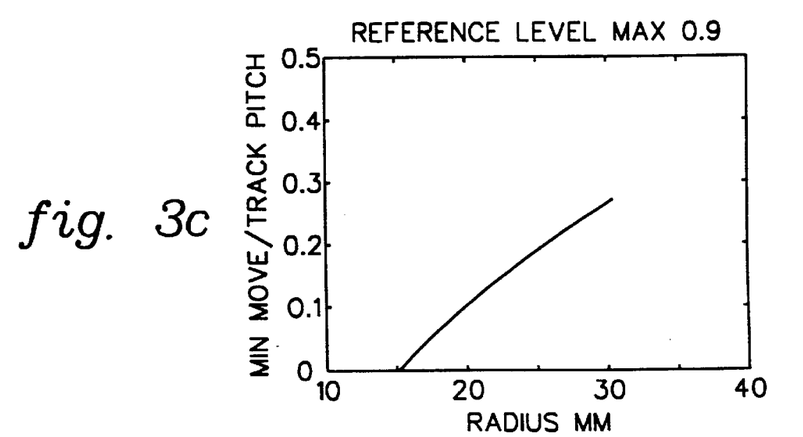
FIGS. 3c and 3d depict changes in the minimum and maximum move distances across the disk surface.
Figure 3D:
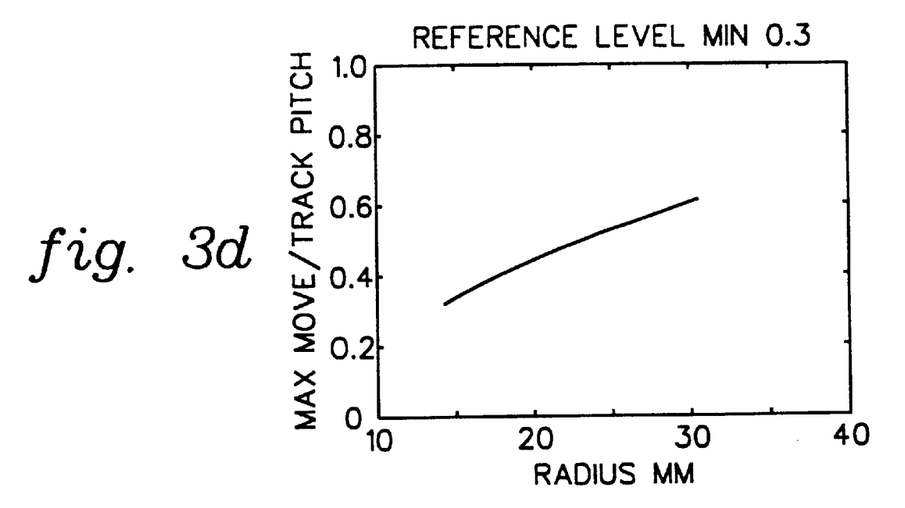
Figure 3E:
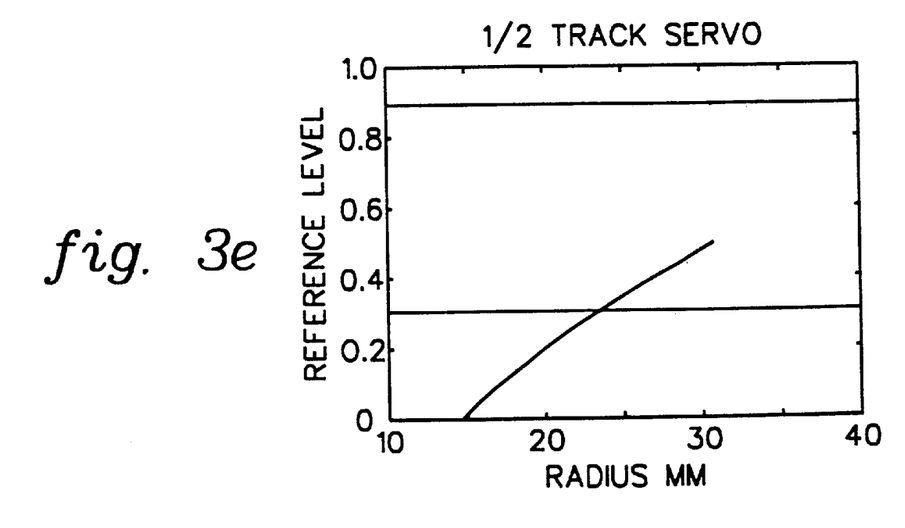
FIG. 3e depicts the usable dynamic range of a reference level for an exemplary desired track spacing (servo track spacing=½ data track spacing) across the disk surface.

The MinimumMove distance is shown in FIG. 3c, and the MaximumMove distance is shown in FIG. 3d for the case of a Reference Level Maximum of 0.9 and a Reference Level Minimum of 0.3. As shown in FIG. 3e, for the case of a minimum servo track pitch equal to ½ of the data track pitch the head would not be able to displace that distance over the entire data radius.

The present invention expands the range of accessible servo track pitches using one, or alternatively a combination of, the following sequences as described below:

Product Servo Track Spacing is Less Than MinimumMove

In the case when the MinimumMove distance exceeds the servo track pitch, several positioning sequences are disclosed to overcome this limit. These three sequences all have in common the feature that bursts outside an immediately preceding track are used while writing. These sequences can be considered either spatial or temporal sequences.

a. Sequence #1

Figure 4:
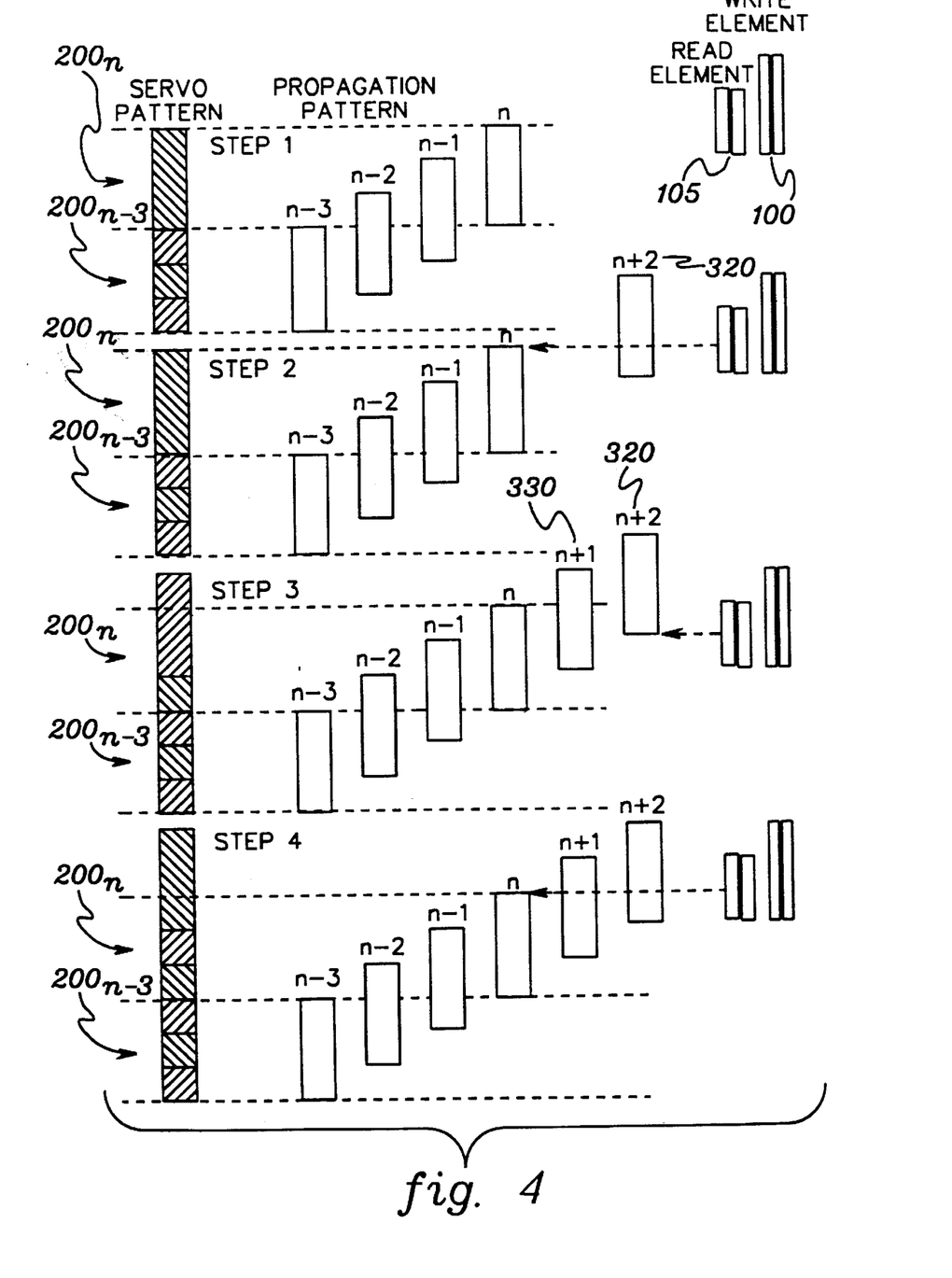
FIG. 4 depicts a first positioning sequence according to the principles of the present invention;.

When the MinimumMove distance exceeds the servo track spacing, head propagation is attained by combinations of larger forward and smaller backward moving steps as shown in FIG. 4. Each step of FIG. 4 having a dotted line shows the self-servowriting process at a point where the head is servoing to a first propagation burst and writing a second propagation burst. A burst, as used herein, broadly connotes any form of physical manifestation, on the disk surface, used to carry information or to position the head (e.g., transition, pulse, pulse train, etc.) The product servo-pattern is shown at the left as a continuous vertical line of data that has been stitched together from repeated writes at the same sector location, for illustrative simplicity. The propagation bursts are shown in the middle with the labels, "n", "n+1", . . . indicating the sequence of propagation bursts at successive radial locations. Tracks 200 are shown corresponding to bursts n and n−3; the overlapping tracks n−1 and n−2 are not shown. (Tracks are merely regions on the medium which generally accommodate a trajectory of bursts.) The collection of tracks $200_{n-3}$ . . . . $200_n$ are referred to herein as a plurality of successive tracks on the medium, and when the terms "preceding" and "succeeding" are used herein, they connote the physical relationship of the tracks unless otherwise explicitly indicated. Track $200_{n-1}$ is "penultimate" to track $200_{n+1}$, and track $200_n$ is between or intermediate these two tracks.

The radial location of the read (105) and write (100) elements is shown at the right, with the dotted line indicating the edge of the reference propagation burst used to generate a succeeding propagation burst. In Step 1, the propagation burst "n" has been written, but the range of motion exceeds the minimum servo track space and therefore the propagation burst n+2 320 is next written (Step 2) by servoing to the outside edge of burst n. In Step 3 the missing propagation burst n+1 330 is written by reversing direction and servoing to the opposite edge of burst n+2. The corresponding product servo-pattern burst n+1 may also be written at this time. This allows the servo-pattern to be written at a smaller step size than the propagation step size. Step 4 illustrates writing the product servo-pattern burst is n+2. The process is then repeated. (It will be understood that the particular sequence of writing the product servo-pattern bursts is generally independent of the sequence in which the corresponding propagation bursts are written. In this example, servo-pattern bursts are written sequentially as would occur in a phase encoded pattern. The propagation bursts however, are not written sequentially.) Thus, when writing bursts n+2, and n+1, the recording head servos on a burst other than that located in an immediately preceding track.

b. Sequence #2

Figure 5:
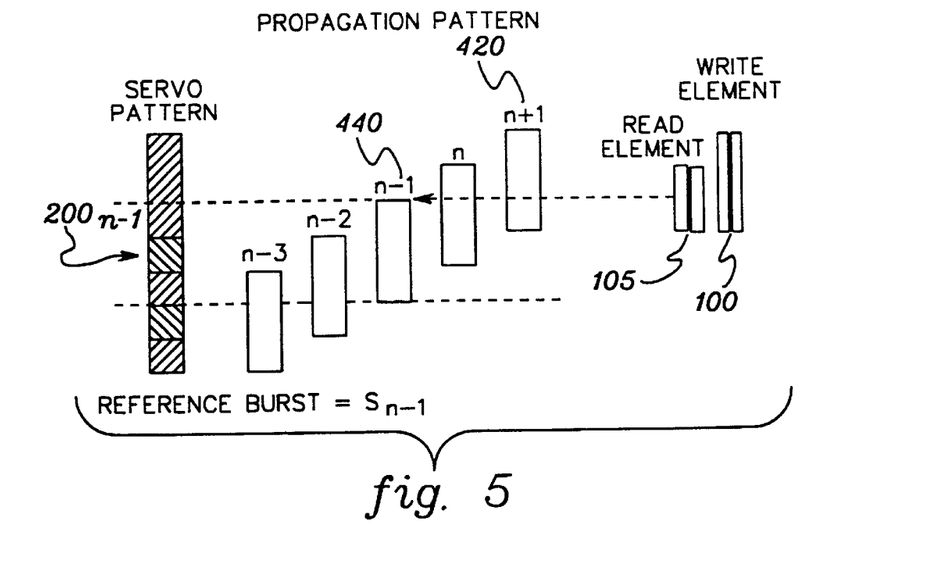
FIG. 5 depicts a second positioning sequence according to the principles of the present invention.

An alternative sequence to solve this limitation is shown in FIG. 5. In this case, when writing propagation burst n+1 420, the recording head can servo on a preceding propagation burst (i.e., in track $200_{n-1}$) other than that located in the immediately preceding track (i.e., $200_n$). As shown in FIG. 5 the head servos to propagation burst n−1 440 (in track $200_{n-1}$), when writing burst n+1 (in track $200_{n+1}$) 420 to allow an increased range of motion. Track $200_{n-1}$ is the track penultimate to track $200_{n+1}$.

c. Sequence #3

Figure 6:
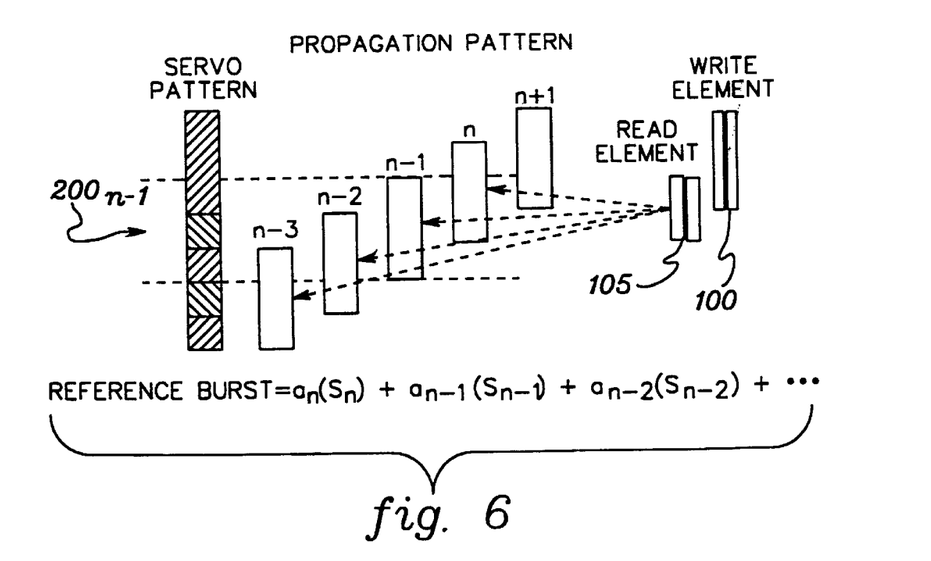
FIG. 6 depicts a third positioning sequence according to the principles of the present invention.

An alternative sequence is shown in FIG. 6. In this case, several bursts n, n−1, n−2 and n−3 are weighted to define a new radial location for propagation burst n+1. An exemplary weighting function is Propagation/Servo Reference level=$a_n(S_n)+a_{n-1}(S_{n-1})+a_{n-2}(S_{n-2})+$
. . . .

where a=weighting coefficients, and S=the burst amplitude or an average amplitude for a burst track. This method may be employed in a manner similar to Sequence #1 in which writing the servo-pattern is delayed by one or more steps of propagation pattern writing with subsequent reversing of servo direction.

It will be understood that writing the servo-pattern may be postponed until after the entire propagation pattern has been written across the entire disk surface.

For Sequence #3, the servo-pattern can be written in a separate process of stepping across the disk using the weighted amplitude burst readings of the propagation pattern to servo to any desired servo track spacing.

One alternative method to overcome changes in reference level required to maintain a fixed propagation burst spacing across the medium, is to fix the reference level to a predetermined value (e.g. 50%) and write propagation burst tracks across the disk surface. The fixed propagation reference level.will result in a variation in the propagation burst track spacing while maintaining a constant reference level within a usable range.

Upon completion of writing propagation burst tracks across the entire disk surface, the recording head is servoed to radial positions derived from the weighted values of the propagation burst amplitudes on more than one track:

Servo Reference Level=$a_n(S_n)+a_{n-1}(S_{n-1})+a_{n-2}(S_{n-2})+a_{n+1}(S_{n+1})+$
$a_{n+2}S_{(n+2)}+$ . . .

wherein S is the average burst amplitude for a propagation burst track and a are the weighting coefficients for that track. Note that since the propagation burst tracks are already written, either or both preceding and succeeding burst tracks can be used in this calculation, or any combination thereof.

Using the calculated servo reference levels, the radial position of the head can be determined and product servo bursts can be written at any desired track spacing. As the propagation burst track spacing is varying, the weighting coefficients will vary in a predetermined manner and generally as a function of radial location across the disk to maintain the desired product servo burst track spacing.

Product Servo Track Spacing is Greater Than MaximumMove

Figure 7:
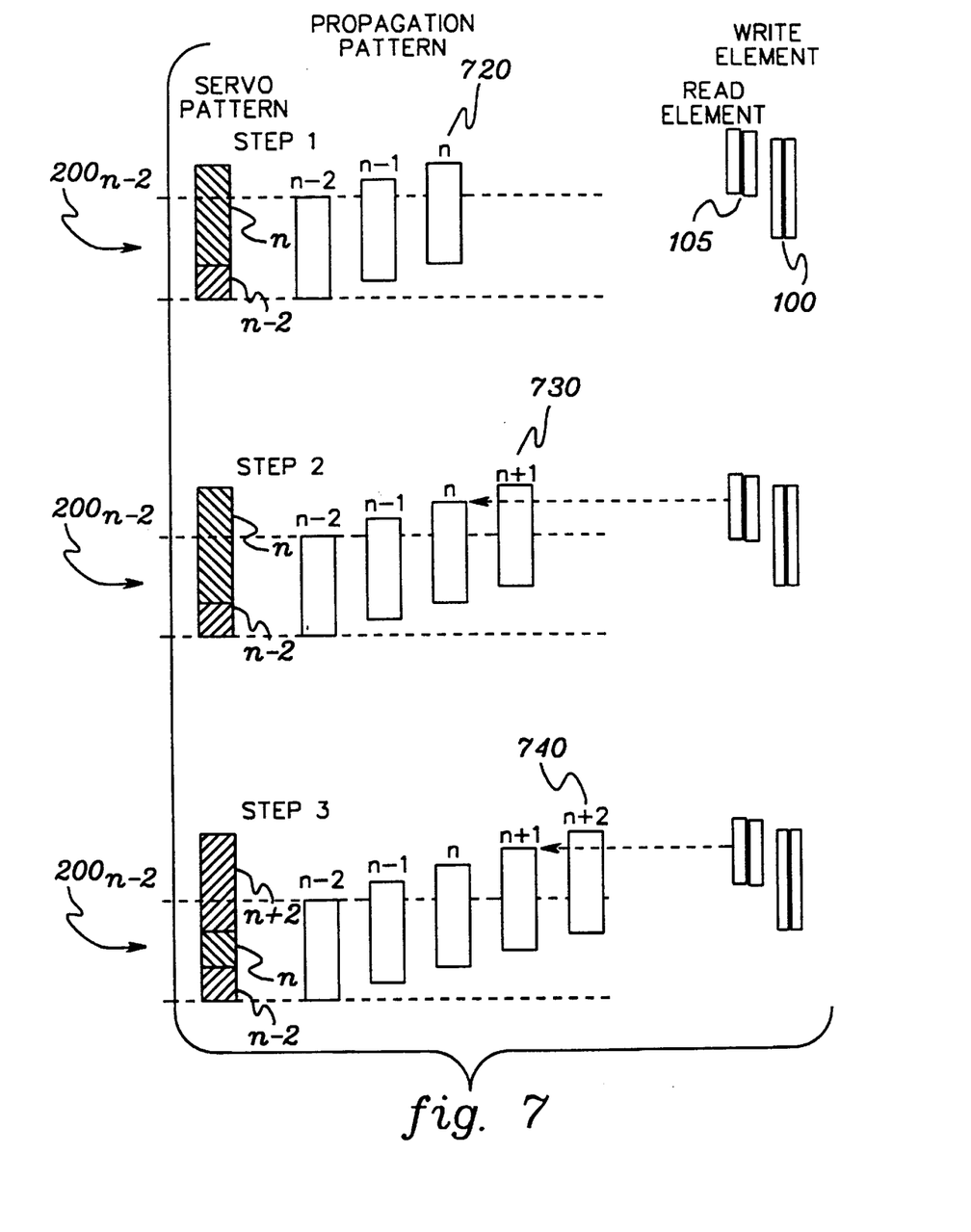
FIG. 7 depicts a fourth positioning sequence according to the principles of the present invention.

In the case when the MaximumMove distance is less than the servo track pitch, a sequence is shown in FIG. 7. The product servo-pattern is written every other propagation step on step n 720 and step n+2 740, but not on intermediate steps n+1 730. Therefore, propagation bursts are written in tracks intermediate the tracks where product servo-pattern bursts are located. This process can obviously be extended to every Nth step N greater than 2.

According to the principles of the present invention, the implementation of these propagation techniques can be selectively applied in the system only when required in certain regions of the surface during the servowriting process to improve the dynamic range. In one embodiment, the techniques associated with FIGS. 4 and 7 are selectively applied to compensate for spacing less than MinimumMove and greater than MaximumMove corresponding to different areas of operation of the heads over the surface. This variation of techniques can take place in an automated fashion in which the reference level is monitored and the techniques adjusted, or it can take place with a priori knowledge of exact techniques needed over respective portions of the disk, depending on the known skew angles, manufacturing tolerances, offsets, etc.

Timing Pattern Propagation

The methods of providing radial pattern propagation bursts were described above. The self-servowrite process includes both the writing of radial patterns and timing or trigger patterns. The propagation of trigger patterns requires a reference level minimum which depends on the signal to noise ratio of the trigger pattern. In certain cases this minimum may be different than the radial requirements for a desired servo-pattern track pitch.

Figure 8A:
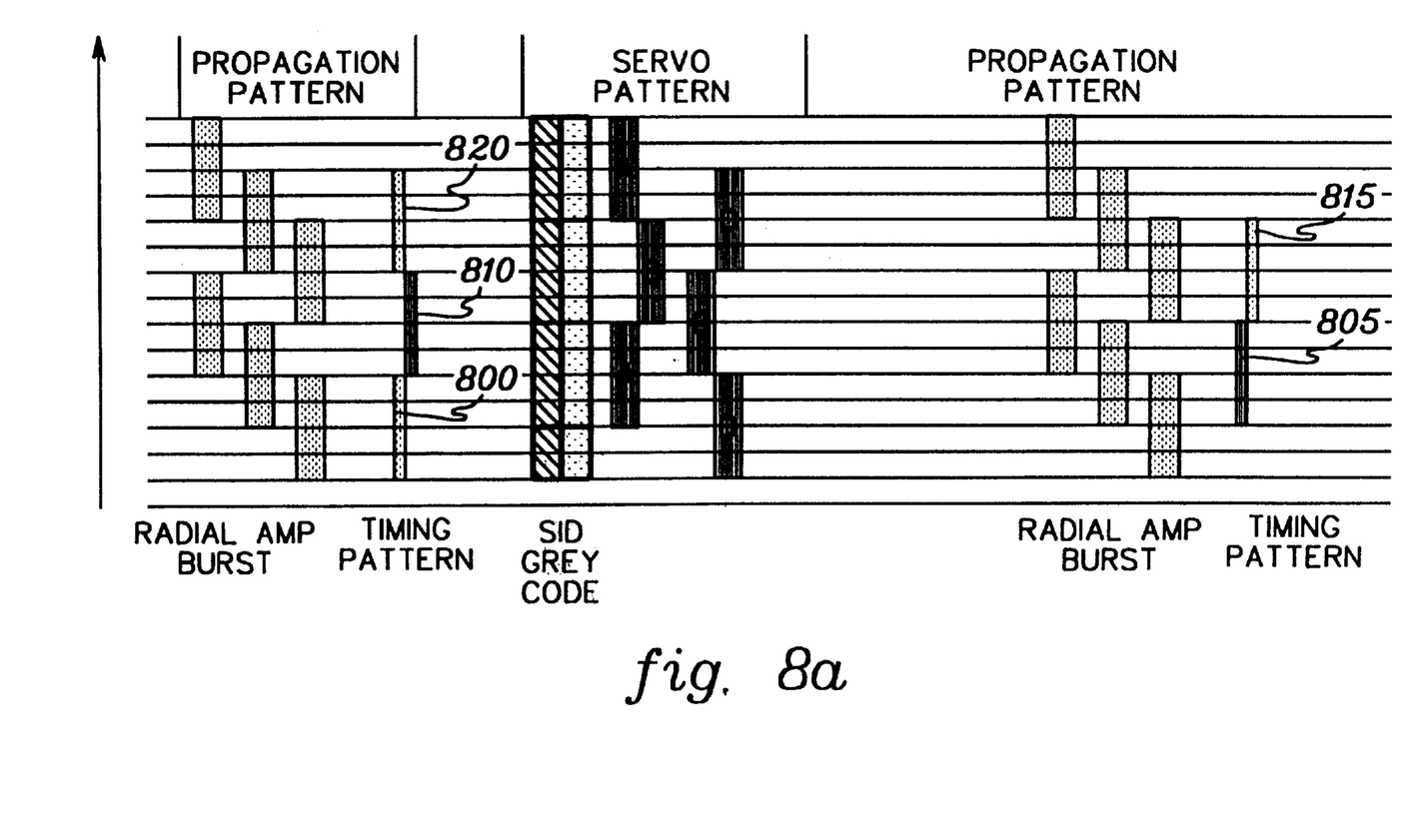
FIGS. 8a–b depict timing pattern and propagation pattern generation according to the principles of the present invention.
Figure 8B:
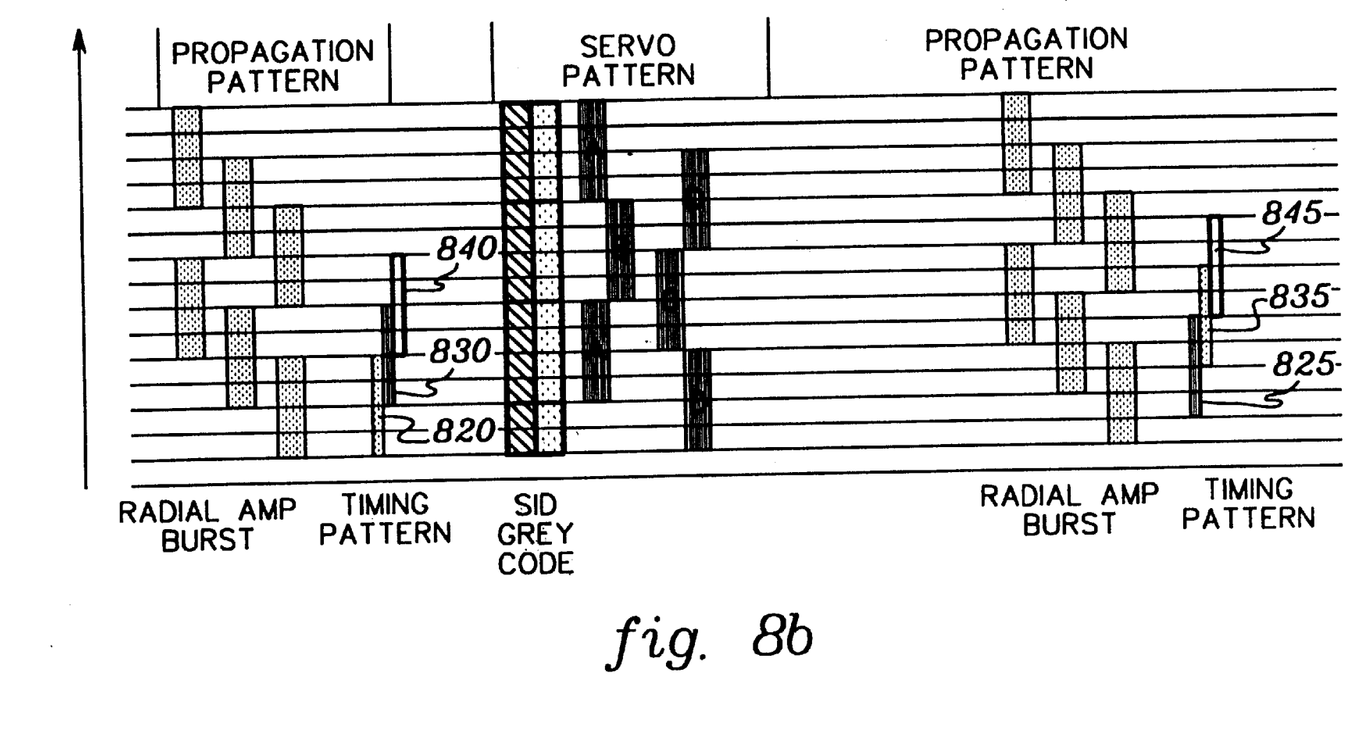

In order to solve this problem, we add one or more additional trigger propagation steps between each servo-pattern write. For example, if the propagation patterns were to be written at ½ track steps, and the amplitude was too low at this pitch, a trigger propagation pitch of ¼ or ⅙ or even ⅛ of a track might be chosen. Servo bursts would only be written at the appropriate steps. As shown in FIG. 8a, the timing patterns 800, 805, 810, 815, 820 are written at the same step size as the radial amplitude propagation patterns of ½ track. In FIG. 8b, the timing patterns 820, 825, 830, 835, 840 are written at ¼ step while the radial propagation bursts are written at ½ step. The trigger propagation only steps could be accompanied by radial propagation steps or simply generated by using a sequence of different reference levels from a single radial propagation step.

Disclosed herein are methods and systems for self-servowriting wherein the reference levels used to create a propagation pattern are kept within a usable dynamic range. In addition to alleviating the need for a complex mechanical and/or optical positioning system to establish servo-patterns on the recording surfaces, the methods and systems solve the problems associated with maximum and minimum reference levels due to manufacturing tolerances, spaced read/write heads, and/or the angular motion of rotary actuators over a recording surface.

It will be understood that the present invention may be applicable to the writing of patterns on any type of storage medium that moves in a repetitive fashion. While such motion may constitute successive rotations of the medium described above, it may also constitute any repetitive or continuous motion including rectilinear and reciprocating motion. Thus, any propagation pattern may be provided over an area of a storage medium using the self propagation. principles described herein.

While the invention has been described in detail herein in accordance with certain preferred embodiments thereof, many modifications and changes therein may be affected by those skilled in the art. Accordingly, it is intended by the following claims to cover all such modifications and changes as fall within the true spirit and scope of the invention.

What is claimed is:

1. A method for keeping a reference signal level in a usable dynamic range, said reference signal level used to position a write head while writing a propagation pattern on a surface of a storage medium of a self-serovwriting system, said method comprising:

using a first positioning sequence for reading and writing a first portion of propagation bursts of said propagation pattern over a first region of said surface; and using a second, different positioning sequence for reading and writing a second portion of propagation bursts of said propagation pattern over a second region of said surface, wherein said reference signal level is kept in the usable dynamic range for positioning said write head while writing said first and second portions of said propagation pattern;

wherein the storage medium comprises a plurality of tracks, and wherein each of the first and second positioning sequences comprises one positioning sequence chose form the following group of positioning sequence:

writing a propagation burst in one track of the plurality of tracks by using propagation bursts located in at least one track preceding and at least one track succeeding said one track to access said on track;

writing a propagation burst in one track of the plurality of tracks while servoing to a second track preceding said one track, said second track not immediately preceding said one track;

writing a propagation burst in one track of the plurality of tracks while servoing to a plurality of propagation bursts located in respective tracks of said plurality of tracks; and servoing to propagation bursts located in respective tracks of a portion of the plurality of tracks to write a plurality of respective product servo-pattern bursts, the respective tracks separated by a distance less than that separating tracks in which said respective product servo-pattern bursts are located.

2. A method of keeping a reference signal level in a usable dynamic range, said reference signal level used to position a write head while writing a propagation pattern on a surface of storage medium of a self-servowriting system, said method comprising:

using a first positioning sequence for reading and writing a first portion of propagation bursts of said propagation pattern over a first region of said surface; and using a second, different positioning sequence for reading and writing a second portion of propagation bursts of said propagation pattern over a second region of said surface, wherein said reference signal level is kept in the usable dynamic range for positioning said write head while writing said first and second portions of said propagation pattern;

wherein the storage medium comprises a plurality of tracks, and wherein one of said first and second positioning sequences comprises writing a propagation burst in one track of the plurality of tracks by using propagation bursts located in at least one track preceding and at least one track succeeding said on track to access said one track.

3. The method of claim 2, wherein the other one of said first and second positioning sequences comprises:

servoing to propagation bursts located in respective tracks of a portion of the plurality of tracks to write a plurality of respective product servo-pattern bursts, the respective tracks separated by a distance less than that separating tracks in which the respective product servo-pattern bursts are located.

4. A system for keeping a reference signal level in a usable dynamic range, said reference signal level used to position a write head while writing a propagation pattern of a surface of a storage medium of a self-servowriting system using only said storage medium and said write head, said system comprising:

means for using a first positioning sequence for reading and writing a first portion of propagation bursts of said propagation pattern over a first region of said surface; and means for suing a second, different positioning sequence for reading and writing a second portion of propagation bursts of said propagation pattern over a second region of said surface, wherein said reference signal level is kept in the usable dynamic range of positioning said write head while writing said first and second portions of said propagation pattern;

wherein the storage medium comprises a plurality of tracks, and wherein each of the first and second positioning sequences comprises one positioning sequence chosen form the following group of positioning sequences:

writing a propagation burst in one track of the plurality of tracks by using propagation bursts located in at least one track preceding and at least one track succeeding said one track to access said one track;

writing a propagation burst in one track of the plurality of tracks while servoing to a second track preceding said one track, said second track not immediately preceding said one track;

writing a propagation burst in one track of the plurality of tracks while servoing to a plurality of propagation bursts located in respective tracks of said plurality of tracks; and servoing to propagation bursts located in respective tracks of a portion of the plurality of tracks to write a plurality of respective product servo-pattern bursts, the respective tracks separated by a distance less than that separating tracks in which said respective product servo-pattern bursts are located.

5. A system for keeping a reference signal level in a usable dynamic range, said reference signal level used to position a write head while writing a propagation pattern on a surface of a storage medium of a self-servowriting system using only said storage medium and said write head, said system comprising:

means for using a first positioning sequence for reading and writing a first portion of propagation bursts of said propagation pattern over a first region of said surface; and means for using a second, different positioning sequence for reading and writing a second portion of propagation bursts of said propagation pattern over a second region of said surface, wherein said reference signal level is kept in the usable dynamic range of positioning said write head while writing aid first and second portions of said propagation pattern;

wherein the storage medium a plurality of tracks, and wherein one of said first and second positioning sequences comprises writing a propagation burst in one track of the plurality of tracks by using propagation bursts located in at least one track preceding and at least one track succeeding said one track to access said one track.

6. The system of claim 5, wherein the other one of said first and second positioning sequences comprises:

servoing to propagation bursts located in respective tracks of a portion of the plurality of tracks to write a plurality of respective product servo-pattern bursts, the respective tracks separated by a distance less than that separating tracks in which the respective product servo-pattern bursts are located.

* * * * *

UNITED STATES PATENT AND TRADEMARK OFFICE
CERTIFICATE OF CORRECTION

PATENT NO. : 6,249,399 B1
DATED : June 19, 2001
INVENTOR(S) : Chainer et al.

It is certified that error appears in the above-identified patent and that said Letters Patent is hereby corrected as shown below:

Column 10,
Line 25, delete "form" and insert -- from --
Line 26, delete "sequence" and insert -- sequences --

Column 11,
Line 19, delete "suing" and insert -- using --

Column 12,
Line 25, after the word medium insert -- comprises --

Signed and Sealed this

Eleventh Day of December, 2001

Attest:

NICHOLAS P. GODICI
*Attesting Officer*     *Acting Director of the United States Patent and Trademark Office*